United States Patent [19]
Matsunaga

[11] Patent Number: 4,788,038
[45] Date of Patent: Nov. 29, 1988

[54] PROCESS FOR KILLING CELLS

[75] Inventor: Tadashi Matsunaga, Fuchu, Japan

[73] Assignee: Kabushiki Kaisya Advance Kaihatsu Kenkyujo, Tokyo, Japan

[21] Appl. No.: 56,305

[22] Filed: Jun. 1, 1987

Related U.S. Application Data

[63] Continuation of Ser. No. 866,493, filed as PCT JP85/00525 on Sep. 20, 1985, published as WO86/01691 on Mar. 27, 1986, abandoned.

[30] Foreign Application Priority Data

Sep. 21, 1984 [JP] Japan ................... 59-196903

[51] Int. Cl.⁴ ............................................. A61L 2/08
[52] U.S. Cl. ..................................... 422/22; 435/173; 210/748; 210/764
[58] Field of Search .................... 422/22, 30, 31; 435/173, 259, 800; 424/90, 133; 252/507, 588

[56] References Cited

U.S. PATENT DOCUMENTS

| | | | |
|---|---|---|---|
| 1,943,633 | 1/1934 | Sperti | 252/588 |
| 2,615,789 | 10/1952 | Davies et al. | 424/133 |
| 3,173,850 | 3/1965 | Hood | 422/22 |
| 3,726,762 | 4/1973 | Puharieh | 435/173 |
| 3,758,257 | 9/1973 | Dastor | 422/31 |
| 3,817,703 | 6/1974 | Atwood | 422/22 |
| 4,071,619 | 1/1978 | Peradze et al. | 424/90 |
| 4,318,883 | 3/1982 | Polony et al. | 422/22 |
| 4,464,336 | 8/1984 | Hiramoto | 422/22 |
| 4,528,270 | 7/1985 | Matsunaga | 435/39 |

FOREIGN PATENT DOCUMENTS

| | | | |
|---|---|---|---|
| 599302 | 6/1960 | Canada | 252/507 |
| 18946 | 8/1964 | Japan . | |
| 31944 | 8/1981 | Japan . | |
| 226534 | 3/1926 | United Kingdom | 435/173 |

OTHER PUBLICATIONS

Chemical Abstracts, CA86 (19):139788g, Studies in the Area of Synthesis and Conversions of Ambidentic and Polydentic Compounds of the Pyridine Series, 1975.

*Primary Examiner*—Benoit Castel
*Attorney, Agent, or Firm*—Finnegan, Henderson, Farabow, Garrett & Dunner

[57] ABSTRACT

The present invention relates to a method for killing cells characterized by bringing a material containing living cells into contact with a non-conductor-carrying photosemiconductor material or a cytocidal material containing the photo semiconductor material and killing the living cells by irradiating light onto the non-conductor-carrying photosemiconductor material, and to a cytocidal agent comprising non-conductor-carrying photosemiconductor material. This non-conductor-carrying photosemiconductor material is relatively inexpensive, since it does not carry a conductor and may be used safely for sterilizing drinking water, food, the human body, and the like because it does not release any poisonous metal ions derived from the conductor in use.

5 Claims, 4 Drawing Sheets

PROCESS FOR KILLING CELLS

This application is a continuation of application Ser. No. 866,493, filed as PCT JP85/00525 on Sep. 20, 1985, published as WO86/01691 on Mar. 27, 1986, now abandoned.

This invention relates to a new and useful process for killing various cells utilizing the voltage generated in a photosemiconductor.

BACKGROUND OF THE INVENTION

The application of germicides, heat and the like has been commonly practiced in order to kill various kinds of cells such as bacteria, microscopic algae, blood corpuscles, and animal and plant cells.

In the treatment of foodstuffs, pharmaceuticals, and various animals and plants, however, these processes have often produced undesirable effects such as denaturation of the material and side effects. In particular, the development of simple and significantly effective cytocidal processes is much sought after in such areas as the sterilization of drinking water, killing algae inhibiting the growth of farm crops, and killing tumorous cells. In Japanese patent application No. 58-221388, the present inventor proposed a process for the selective control of cellular activity by the application of a prescribed voltage to cells. This process involves applying scanning electric potentials on cells, using techniques such as cyclic voltammetry, differential polarography, and phase discrimination AC polarography to obtain measured values of the electric currents generated. The process enables cellular activities such as respiratory activity to be selectively and effectively inhibited and controlled by externally applying to the cells an electric potential that is close to the value of a potential giving the ultimate value characteristic to cells of the current-potential curve or the ultimate value of a differential electric current (peak potential value), and furthermore, it enables bactericidal or antimicrobial control to be achieved. Taking advantage of this principle, a process that comprises allowing photosemiconductors such as $TiO_2$ and the like to carry conductors such as Pt and the like, and utilizing the photoelectromotive force generated by these particles to directly apply said peak potential to various cells to kill them has been proposed. Each of these cytocidal processes uses a photosemiconductor carrying a conductor. Such cytocidal processes using conductor-carrying photosemiconductors are, however, not completely satisfactory. For example, where metals other than platinum are used as conductors, since they are liable to elute into the material subjected to sterilization while in use, these metals cannot be used for such purposes as the sterilization of drinking water. On the other hand, where platinum is used as a conductor, the cost of cell-killing is exorbitant because it is an expensive metal. For these reasons, a cytocidal process which does not impart metals to the material under cytocidal treatment and can be implemented at a low cost is much sought after.

SUMMARY OF THE INVENTION

This invention provides a method for killing cells characterized by bringing a material containing living cells into contact with a non-conductor-carrying photosemiconductor material or a cytocidal agent containing this material, and killing the living cells by the irradiation of light to the non-conductor-carrying photosemiconductor. Upon irradiation of the non-conductor-carrying photosemiconductor material, a voltage is generated in the semiconductor which is then applied to the cells to kill them.

DESCRIPTION OF THE PREFERRED EMBODIMENT

(Types of Cells Killed)

The process of the present invention is able to kill various microorganisms such as bacteria, actinomycetes, molds, microscopic algae and yeasts, animal cells such as red and white corpuscles, tumorous cells, and tissue-culture cells and plant cells.

(Non-Conductor-Carrying Photosemiconductor Material)

Although all semiconductor materials possess the Dember effect, the photoelectromotive force is proportional to the logarithm of the electron-positive hole mobility ratio, with the photoelectromotive force being "zero" when the logarithm is one. Accordingly, $TiO_2$, $R_uO_2$, $Cs_3Sb$, InAs, InSb, and GaAs with relatively high electron-positive hole mobility ratios may be cited as suitable semiconductor materials for actual use.

(Mode of Operation for The Cytocidal Process)

Where the materials subject to treatment are relatively transmissible liquids such as drinking water and brine, the semiconductor material may be introduced directly into these materials and the cells contained in them, e.g., microorganisms may be killed by irradiating the semiconductor material. This irradiation may be carried out from the outside of the liquids and also may be carried out with a submerged light source. Where the semiconductor material is used in the field for such purposes as the killing of algae, no artificial light source is required as sunlight is usually utilized. After cytocidal treatment, the sterile product is obtained by removing the semiconductor material using conventional methods such as filtration and centrifugation. The recovered semiconductor material also may be repeatedly reused.

In order to kill microorganisms present on the surface of the skin and the like, the killing may be accomplished by applying the cytocidal agent of the present invention to such subjects and irradiating the cytocide. In this case various preparations such as powder, gel, sol, and ointment may be used as the cytocidal agents mentioned above. The powder preparation may be made by blending particles of the non-conductor-carrying photosemiconductor material with talc, zinc stearate, starch and the like. The ointment preparation may be made by blending particles of the non-conductor-carrying photosemiconductor material with excipients such as petrolatum, paraffin, vegetable oil, and starch paste. Being transparent, superfine particles of $TiO_2$ are especially suitable for use as a sol type cytocidal agent.

Figure 2:
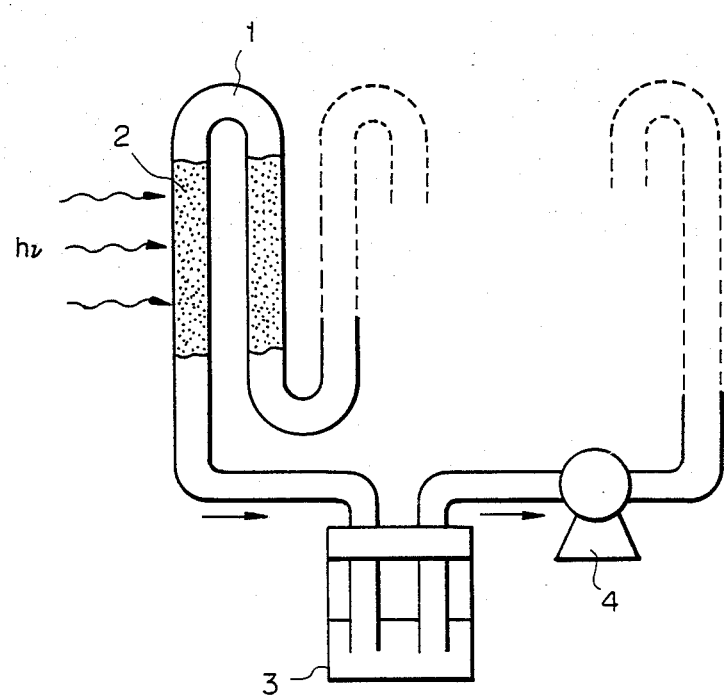
FIG. 2 is a schematic sectional view of the sterilizer used in Example 4 which uses the solid type cytocidal agent of the present invention.

In addition, the cytocidal process of the present invention permits the use of a solid type cytocidal agent in which the non-conductor-carrying photosemiconductor material is immobilized to a carrier. As illustrated in FIG. 2, in one of the preferred embodiments of the process of the present invention a column is filled with the solid type cytocidal agent and the liquid to be treated is continuously passed through the column and thus a sterilized liquid free from the photosemiconductor material can be obtained continuously. This process is extremely practical. In FIG. 2, the glass tube 1 is packed with the solid type cytocidal agent 2 carrying fine particles of the photosemiconductor, and this portion of the glass tube is irradiated externally through the wall. Both ends of the glass tube (1) connect to liquid reservoir (3) allowing the apparatus to form a circulatory system as a whole. The liquid to be treated is circulated by the pump (4) and sterilized by the fine particles of the photosemiconductor on passing through the solid type cytocidal agent (2).

The apparatus illustrated uses transparent glass for the main frame portion, but when non-transparent materials such as plastic, cement, metal, etc., are used for this portion, a light source should be provided within the apparatus. Xenon lamps, metal halide lamps, and fluorescent lamps may be suitably used as light sources, but it is also possible to introduce light into the apparatus from outside sources, such as sunlight, using optical fiber. As solid carriers for the solid type cytocidal agent, nitrocellulose, glass, polyvinyl chloride, plastic, nylon, methacrylic resin, and polypropylene may be used and the size and form of the carrier may be suitably selected according to the type of apparatus and the kind and nature of the material subject to be treated. For example, film, beads, board, and fiber are some conceivable forms of the carrier.

(Sources of Irradiation)

Both natural light (sunlight) and artificial light may be used as light sources for the killing of cells. Incandescent lamps, fluorescent lamps, sun lamps, xenon lamps, and metal halide lamps may be used as artificial light sources. The following examples further illustrate the cytocidal effect of the cytocidal process and cytocidal agents of the present invention as well as details of practical use.

EXAMPLE 1

Powdered $TiO_2$ (P-25, Nippon Aerosil Ltd.) was used as the fine particles of the non-conductor-carrying photosemiconductor. After culturing for 12 hours, a liquid culture medium containing cells of *E. coli* was diluted to $2.5 \times 10^5$ cells/ml and to 4 ml of this suspension was added 3.2 ml of fine particles of the non-conductor-carrying photosemiconductor. The mixture was then irradiated with a 400W sun lamp or a 300W xenon lamp (luminous intensity of 1000 $\mu E/m^2 \cdot sec.$). A viable cell count was made by the colony counting method. For comparison, viable cell counts were made for the control suspensions, viz. a suspension similarly prepared without fine particles of the non-conductor-carrying photosemiconductor and subjected to irradiation and a suspension prepared with said fine particles and not subjected to irradiation. The sterility was also investigated during another experiment in which the fine particles of the non-conductor-carrying photosemiconductor were kept from coming into direct contact with the cells by a dialysis membrane.

The results showed that 50% of the *E. coli* cells had been killed at 40 minutes and 100% at 90 minutes on irradiation in the presence of fine particles of the non-conductor-carrying photosemiconductor, whereas no sterilization effect was observed in other cases. The negative result of the experiment in which the cells were segregated from the non-conductor-carrying photosemiconductor showed that the sterilization effect is not ascribed to the influence of a substance formed by photocatalytic reaction. Microscopic observations of the cells after 90 minutes of irradiation in the presence of the non-conductor-carrying photosemiconductor showed no sign of cell aggregation or cell membrane damage, but showed instead a decrease in CoA (coenzyme A) within the cells. This suggested that the sterilization had been effected by electron transfer reaction of the fine particles of the non-conductor-carrying photosemiconductor and the cells. It has thus been shown that sterilization is effected on the mechanism similar to that of the electrode system by the use of fine particles of the non-conductor-carrying photosemiconductor.

EXAMPLE 2

Figure 1:
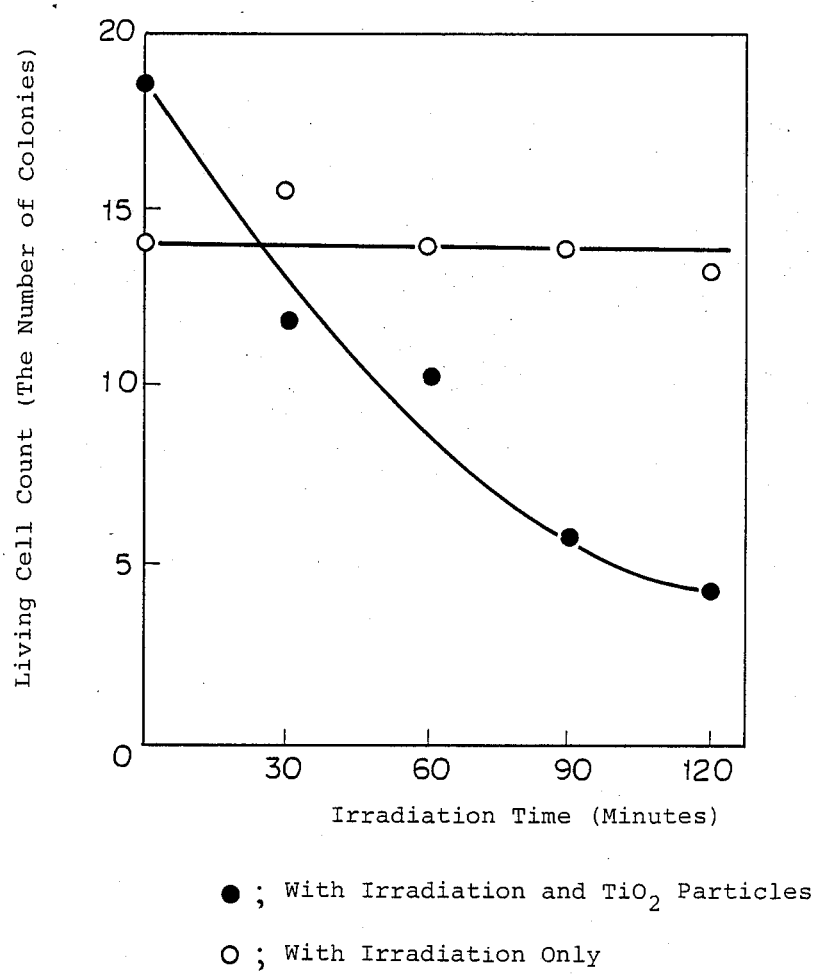
FIG. 1 is a graph representing the relationship between the irradiation time and the viable cell count obtained in Example 2 using Baker's yeast, *S. cerevisiae* cells.

Powdered $TiO_2$ (P-25, Nippon Aerosil Ltd.) of the anatase type was used as a non-conductor-carrying photosemiconductor. A strain of *S. cerevisiae* was cultured under aerobic conditions for 12 hours, and after collection of the cells, the cells were suspended in a 0.1M phosphate buffer (pH 7.0). The cell concentration of the suspension was adjusted using a hemacytometer and to this was added powdered $TiO_2$ at a $10^4$ cells/mg concentration. The mixture was irradiated and cell counts were made for 120 minutes at 30-minute intervals. Powdered $TiO_2$ was also added to the suspension at a $10^4$ cells/mg concentration and at a $10^3$ cells/mg concentration, and after 90 minutes of irradiation cell counts were made. A 400W sun lamp (luminous intensity of 1400 $\mu E/m^2$ sec.) or a 300W xenon lamp (luminous intensity of 1000 $\mu E/m^2$ sec.) was used for the irradiation. All cell counts were made using the colony counting method. The results showed that about 50% of the population had been killed and about 70% killed, respectively, after 60 minutes and 90 minutes of irradiation at a powdered $TiO_2$ concentration of $10^4$ cells/mg as illustrated in FIG. 1. About 50% was killed at a powdered $TiO_2$ concentration of $10^3$ cells/mg and about 90% killed at a concentration of $10^4$ cells/mg cell after 90 minutes of irradiation.

The respiratory activity of cells was measured on the basis of the decrease in the value of the current of the oxygen electrode. The CoA in the cells was also measured by the enzyme analysis method using phosphotransacetylase. The results showed signs of respiratory activity inhibition with the increase in the length of irradiation time as well as declines in the amount of CoA in the cells.

Morphological observations of the irradiated cells by an electron microscope showed changes in the structure of the cell wall as well as cell aggregations at high cellular concentrations.

Viable cell counts made after covering powdered $TiO_2$ with a dialysis membrane so that the cells would not come into direct contact with the powdered material, showed no decline.

Powdered $TiO_2$ in an amount of 0.01 gram was suspended in 40 ml of CoA solution (0.1 mM) and the suspension was irradiated for 90 minutes with a sun lamp (1400 $\mu E/m^2$ sec ). The result showed the decrease of the CoA amount to 0.04 mM. Analysis of irradiated solutions by thin layer chromatography for reaction products suggested that the oxidation product of CoA could be a CoA dimer.

It can be assumed from the above results that the mechanism of sterilization of yeast by the non-conductor-carrying photosemiconductor is similar to that by the electrode wherein CoA in the cell is oxidized on the surface of powdered $TiO_2$ and the respiratory activity of the cell is inhibited by the resulting oxidation product, and changes in the structure of the cell wall are brought about by the reaction of CoA.

EXAMPLE 3

Powdered $TiO_2$ (P-25, Nippon Aerosil Ltd.) was used as fine particles of the non-conductor-carrying photosemiconductor. Green algae *Chlorella vulgaris* and blue-green algea *Synechococcus sp.* were used as targets of the cytocidal experiments. Five milligrams of powdered $TiO_2$ was added to 5 ml of cultured broth of *Chlorella vulgaris* ($10^7$ cells/ml) and the suspension was irradiated with a 400W sun lamp or a 300W xenon lamp (luminous intensity 1000 $\mu E/m^2$ sec). The irradiated cells was adsorbed and immobilized on the surface of a membrane filter and the filter was attached to the oxygen electrode. The photosynthetic ability of green algae was measured on the basis of oxygen production under irradiation. The respiratory activity was then measured on the basis of oxygen uptake on the addition of glucose under dark conditions. After 2 hours of irradiation, declines were observed in the algae's pholosynthetic and respiratory activities.

On the other hand, no declines in these parameters were observed in all other runs without the addition of fine particles of the non-conductor-carrying photosemiconductor and without irradiation.

Powdered $TiO_2$ was added to each of the suspensions containing *Chlorella vulgaris* cells at different concentrations and the cells were microscopically observed after 2 hours of irradiation. Observation of the irradiated suspension with the cell concentration of $10^7$ cells/ml showed that *Chlorella vulgaris* cells were attached to $TiO_2$ particles forming lumps. With the cell concentrations of $10^5$ cells/ml and $10^3$ cells/ml, no such lamps were observed. In all cases, no damage to the cell wall was observed.

A cultured broth containing *Chlorella vulgaris* cells was diluted to various concentrations and to the resulting suspensions was added powdered $TiO_2$. After irradiation of the mixtures, viable cell counts were made by the colony counting method. That is, addition amounts of powdered $TiO_2$ were varied according to the cell count of individual suspensions ranging in cell concentrations from $10^3$ cells/ml to $10^5$ cells/ml, and viable cell counts were made after 2 hours of irradiation. The rates of decrease in the number of colonies were 33% and 40% respectively for mixtures with the $TiO_2$ concentrations of $2.1 \times 10^4$ cells/mg semiconductor and $2.1 \times 10^3$ cells/mg semiconductor. Thus the cytocidal effect was dependent upon the cell concentration and the cell count per unit of non-conductor-carrying photosemiconductor particles. Similar results were obtained with *Synechococcus sp.*

The above results suggested that the killing algae is possible by photocatalytic reaction of the non-conductor-carrying photosemiconductor particles. The lesser cytocidal effect of the non-conductor-carrying photosemiconductor particles on *Chlorella vulgaris* as compared to those on bacteria and yeast is attributed to the thick wall that protects the cells.

EXAMPLE 4

0.1 gram of nitrocellulose was dissolved in 3 ml of acetone and the solution was used to prepare a semidry film having a surface area of 14 $cm^2$. 40 milligrams of $TiO_2$ particles (P-25, Nippon Aerosil Ltd.) were adhered to the film and this was dried to prepare a solid $TiO_2$ film. This solid film was coiled into a spiral form and was inserted into the column of the sterilizer illustrated in FIG. 2.

Figure 3:
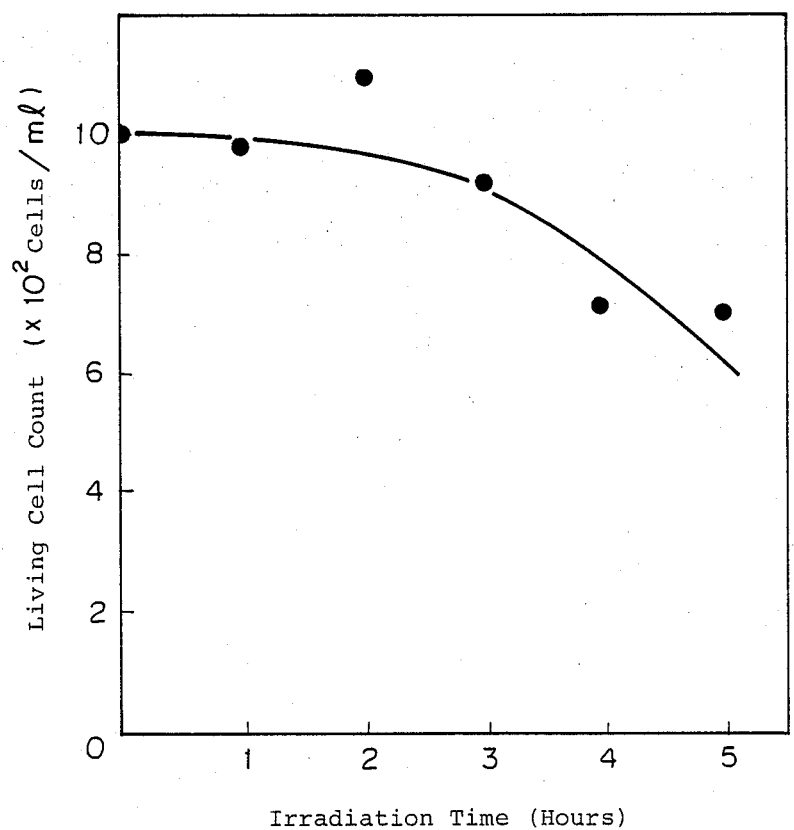
FIG. 3 is a graph representing the relationship between irradiation time and the viable cell count obtained using *E. coli.*.

A cultured broth containing *E. coli* cells was diluted to a cell concentration of $1.0 \times 10^3$ cells/ml and 50 ml of the cell suspension was sterilized on said apparatus loaded with four solid $TiO_2$ films (160 mg of $TiO_2$). The flow rate was set at 300 ml/n and a xenon lamp (luminous intensity $1.2 \times 10^4$ $\mu E/m^2$ sec.) was used as a light source. Consequently 10% and 30% of the cell population were shown to have been killed after 180 minutes and 300 minutes of irrddiation respectively. The results are summarized in FIG. 3, in which the viable cell count per milliliter is plotted as the ordinate and the irradiation time is plotted as the abscissa.

Figure 4:
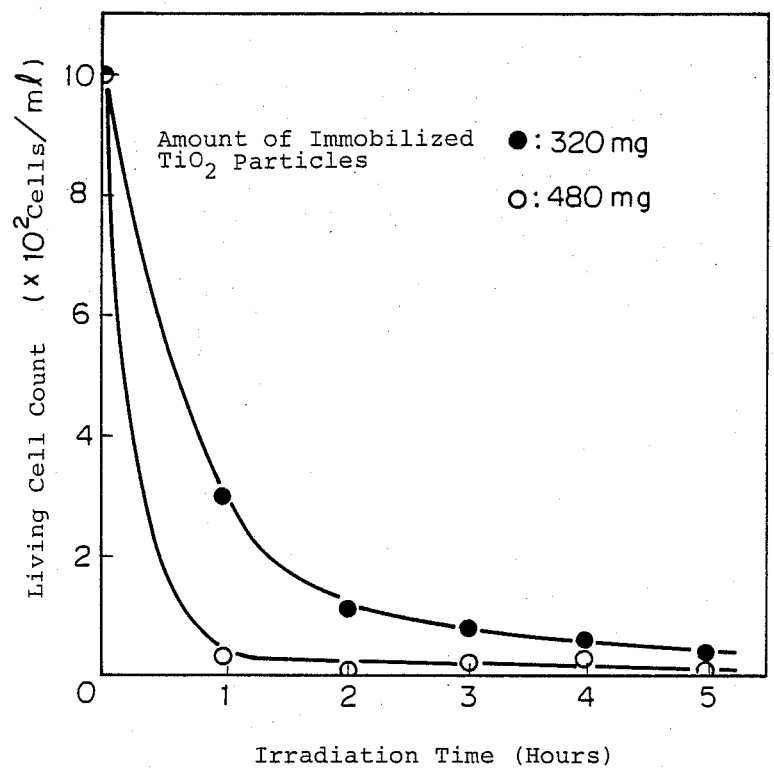
FIG. 4 is a graph representing the relationship between the irradiation time and the viable cell count similar to FIG. 3. The amount of the solid type cytocidal agent used and the flow rate of the liquid treated in Example 3 are different from those of Example 4.

Another experiment in which eight solid $TiO_2$ films (320 mg $TiO_2$) were used with the flow rate set at 150 ml/h and other conditions remaining the same showed improvements in cytocidal efficiency, i.e., 70% and 90% after 60 minutes and 180 minutes of irradiation respectively. In still another experiment with twelve solid $TiO_2$ films, cytocidal efficiencies as high as 95% and 100% at 60 minutes and 300 minutes respectively were achieved. These results are summarized in FIG. 4 in which the viable cell count per milliliter is plotted as the ordinate and the irradiation time is plotted as the abscissa. In control experiments run parallel to said experiments without using solid $TiO_2$ films, no declines in the viable cell count were observed.

As is evident from the above results, this invention enables cytocidal treatment at a low cost without undesirable effect on the treated product.

I claim:

1. A method of killing cells comprising the steps of placing living cells in contact with a non-conductor carrying photosemiconductor material and irradiating light to said non-conductor carrying photosemiconductor material to generate a photoelectromotive force, so as to kill said cells.

2. The method of claim 1, wherein said living cells are contained in an aqueous liquid and the contact between said photosemiconductor material and said aqueous liquid is made by suspending said photosemiconductor material in said aqueous liquid.

3. The method of claim 2, which further includes the step of separating said photosemiconductor material from said aqueous liquid after the cells have been killed.

4. The method of claim 1, wherein said living cells are contained in an aqueous liquid and said photosemiconductor material is immobilized with an insoluble carrier to form a solid type photosemiconductor material, the contact between said solid type photosemiconductor material and said aqueous liquid being made by passing said aqueous liquid through a column filled with said solid type photosemiconductor material.

5. The method of claim 1, wherein said photosemiconductor material is selected from the group consisting of $TiO_2$, $RuO_2$, $Cs_3Sb$ and GaAs.

* * * * *